(12) United States Patent
Baccelli et al.

(10) Patent No.: US 7,998,211 B2
(45) Date of Patent: Aug. 16, 2011

(54) INTERVERTEBRAL DISK PROSTHESIS PROVIDED WITH ANCHOR MEANS

(75) Inventors: Christian Baccelli, Saucats (FR); Karl Belliard, La Membrolle sur Longuenee (FR)

(73) Assignee: Zimmer Spine S.A.S., Bordeaux (FR)

( * ) Notice: Subject to any disclaimer, the term of this patent is extended or adjusted under 35 U.S.C. 154(b) by 607 days.

(21) Appl. No.: 11/995,126

(22) PCT Filed: Jul. 17, 2006

(86) PCT No.: PCT/FR2006/050720
§ 371 (c)(1),
(2), (4) Date: Oct. 17, 2008

(87) PCT Pub. No.: WO2007/010161
PCT Pub. Date: Jan. 25, 2007

(65) Prior Publication Data
US 2009/0132052 A1    May 21, 2009

(30) Foreign Application Priority Data

Jul. 18, 2005    (FR) ..................................... 05 07580

(51) Int. Cl.
*A61F 2/44* (2006.01)
(52) U.S. Cl. .................................................. 623/17.15
(58) Field of Classification Search ..... 623/17.11–17.16
See application file for complete search history.

(56) References Cited

U.S. PATENT DOCUMENTS

| 5,609,635 | A  | 3/1997 | Michelson |
| 6,179,873 | B1 | 1/2001 | Zientek |
| 2004/0002759 | A1 | 1/2004 | Ferree |

FOREIGN PATENT DOCUMENTS

| WO | 2007/010161 A2 | 1/2007 |
| WO | 2007/010161 A3 | 1/2007 |

OTHER PUBLICATIONS

International Search Report and Written Opinion for PCT/FR2006/050720, completed Jan. 15, 2007, mailed Jan. 24, 2007, 10 pgs.).
English translation of the Written Opinion for PCT/FR2006/050720, completed Jan. 15, 2007, mailed Jan. 24, 2007, 6 pgs.).
International Preliminary Examination Report for PCT/FR2006/050720, issued Jan. 22, 2008, 7 pgs.
English translation of the International Preliminary Examination Report for PCT/FR2006/050720, issued Jan. 22, 2008, 7 pgs.

*Primary Examiner* — Thomas C. Barrett
*Assistant Examiner* — Sameh Boles
(74) *Attorney, Agent, or Firm* — Sprinkle IP Law Group

(57) ABSTRACT

An intervertebral disk prosthesis is provided. The prosthesis comprises: a first plate for engaging a first vertebral body, said first plate comprising a first slot formed through the first plate; a second plate for engaging a second vertebral body, said second plate comprising a second slot formed through the second plate; a first anchor member, said first anchor member positioned and slidable through the first slot and having a sharp edge for penetrating into the first vertebral body; and a second anchor member, said second anchor member positioned and slidable through the second slot and having a sharp edge for penetrating into the second vertebral body. The first plate and the second plate engage with one another by way of complimentary concave and convex spherical cap portions to provide relative movement between the first plate and the second plate.

16 Claims, 4 Drawing Sheets

INTERVERTEBRAL DISK PROSTHESIS PROVIDED WITH ANCHOR MEANS

This application is the National Stage of International Application No. PCT/FR2006/050720, filed on Jul. 17, 2006, which claims priority to French Patent Application Number 0507580, filed on Jul. 18, 2005, the contents of both of which are hereby are incorporated by reference as if fully set forth herein.

The present invention relates to an intervertebral disk prosthesis provided with anchor means.

When a natural intervertebral disk has suffered significant degeneration, it is necessary to remove it and replace it with a mechanical prosthesis. As a general rule, such mechanical prostheses are made up of two elements, each element having an anchor face for anchoring in the vertebral plate of a vertebra and a co-operation face, where the co-operation faces respectively define a concave spherical cap portion and a convex spherical cap portion. The assembly thus constitutes a ball joint system that conserves for the patient the ability to perform relative movements between the two vertebrae between which the prosthesis is installed. The top and bottom elements making up the prosthesis may be single pieces, or each of them may be made up of a first part forming a prosthetic plate that is to come into contact with the vertebral plate, which part is associated with an insert that defines the concave or convex spherical cap portions.

The present invention applies to both types of intervertebral disk prostheses describes above, or to an intermediate version in which one of the prosthesis elements is a single piece and the other includes an insert.

In addition, each prosthetic plate needs to have an anchor face that is anchored in the vertebral plate. The anchor members are constituted by portions in relief projecting from the anchor face of the prosthetic plate. These portions in relief may be of various kinds, for example they may be constituted by serrations or ribs or by larger portions in relief, e.g. presenting the shape of a triangular spur. To obtain strong anchoring in the vertebral plate, it is necessary for the anchor member to present a size that is sufficient in the direction orthogonal to the anchor face of the prosthetic plate. This anchor member therefore increases the thickness of the prosthetic plate relative to the dimensions that correspond to the functional requirements of the plate for mechanical strength.

It is known that it is important to limit the spacing between the two vertebrae between which it is desired to install the intervertebral implant. The greater this spacing, the more the various ligaments interconnecting the vertebrae are stretched temporarily and thus the more they are traumatized.

It is also important for the anchor elements to be effective in performing their function of a projecting element that penetrates into the vertebral plates.

Finally, it is most desirable for the structure of the anchor elements not to increase the difficulty for the surgeon when placing the implant between the vertebrae.

An object of the present invention is to provide an intervertebral disk prosthesis presenting at least one anchor member of large size but without significantly modifying the dimensions of the prosthetic plate, and that is effective without impeding the surgeon while putting the implant into place.

To achieve this object, the intervertebral disk prosthesis comprises:

a first assembly comprising a prosthetic plate having a fastener face provided with anchor members for anchoring in a vertebra; and a second assembly comprising a prosthetic plate having a fastener face provided with anchor members for anchoring in another vertebra;

said prosthesis being characterized in that each anchor member comprises:

a slot formed in a prosthetic plate and passing right through it;

an anchor member mounted on said slot, said element having at least a portion of size greater than the height of said slot;

means forming a pivot axis XX' for pivoting said anchor element relative to the prosthetic plate, whereby said anchor element can be moved from a rest, first position in which said anchor element does not project from the fastener face of the prosthetic plate, towards an active, second position in which at least a portion of said anchor element projects from the fastener face of the prosthetic plate;

first holder means for holding in said first position; and second holder means for holding in said second position.

It will be understood that the fact that the anchor member is pivotally mounted in the slot formed in the prosthetic plate enables the anchor member to occupy an initial position while the prosthesis is being put into place in which it projects from the co-operation face of the prosthetic plate and not from its anchor face. Thus, in this position, the presence of the anchor member does not significantly increase the thickness of the top or bottom element of the prosthesis because the co-operation faces of these elements have parts defining concave and convex spherical cap portions respectively that themselves necessarily project from the prosthetic plate. In contrast, when the surgeon causes the anchor members to pivot into the vertebral plate, the projecting portion of the anchor member can be larger in order to provide effective anchoring.

In addition, because of the presence of the first holder means for holding in the first position, the prosthesis element is easy for the surgeon to put into place since the anchor member is held in this position. It will also be understood that when the surgeon seeks to move the anchor member into its active, second position, the anchor member is effectively locked in the second position by the second holder means, so the anchor member performs its function effectively.

Preferably, said anchor element has a second end having said first and second holder means, and a first end shaped to co-operate with a portion of the wall of said slot to define said means forming a pivot axis.

Also preferably, said anchor element is of substantially constant thickness in the direction of the means forming the pivot axis, and said anchor element presents a dimension in the height direction of the slot that decreases going from its second end towards its first end.

Also preferably, said second end of the anchor element has a first portion suitable for co-operating by wedging with a second portion of the wall of said slot opposite from the portion defining the means forming the pivot axis and forming said first holder means, and a second portion that is elastically deformable defining a recess suitable for co-operating with said second portion of the wall of the slot to form the second holder means.

Other characteristics and advantages of the invention appear better in the light of the following description of a preferred embodiment of the invention given by way of non-limiting example. The description refers to the accompanying figures, in which.

Figure 1:
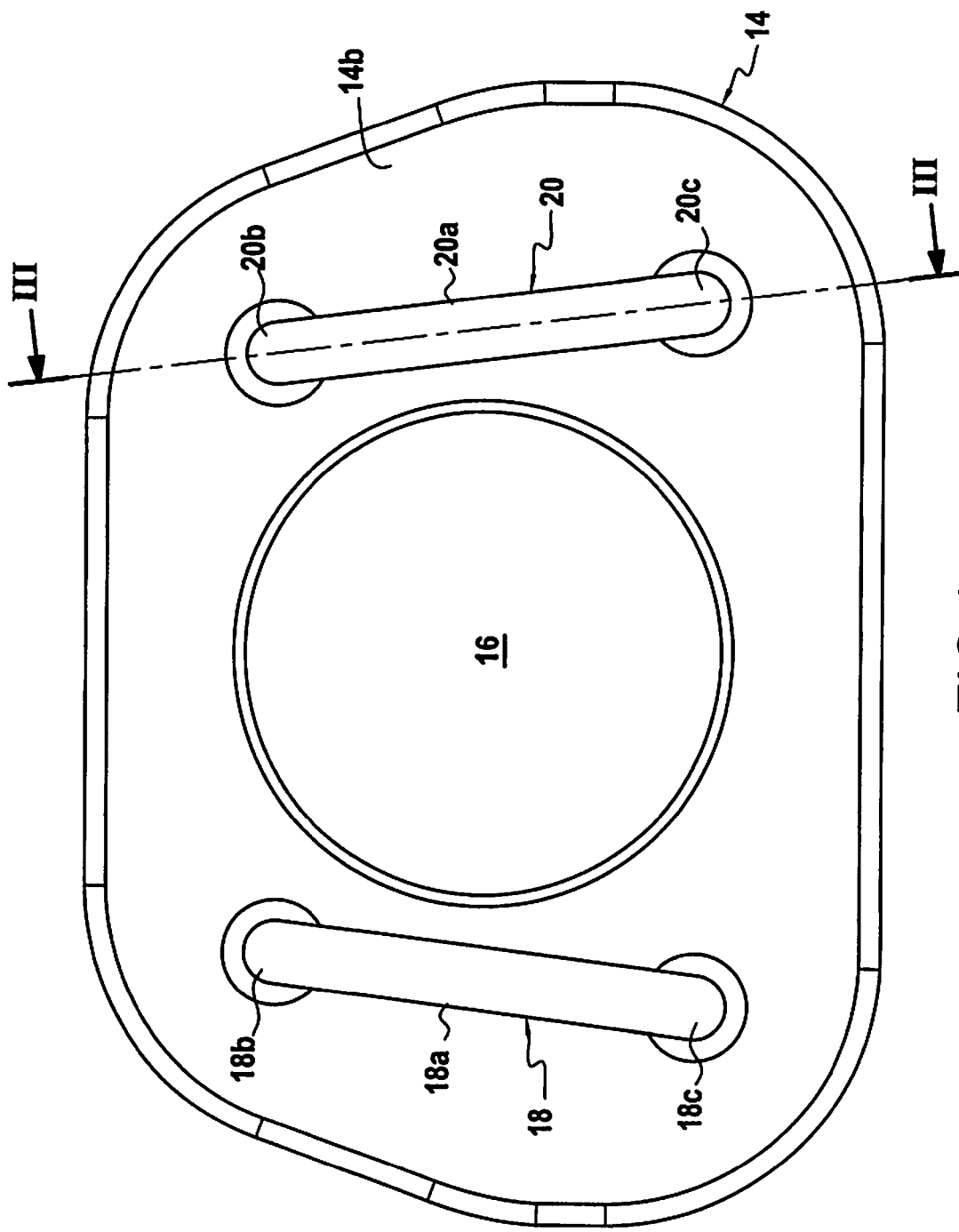
FIG. 1 is a simplified plan view of a prosthesis element.

FIG. 1 is a simplified diagram showing the bottom prosthesis element 10. It comprises a prosthetic plate 14 of generally trapezoidal shape having an anchor face 14a (not visible in the figure) and an active 14b. In the active face 14b, there is defined a surface forming a portion of a concave spherical cap 16. The prosthetic plate 14 includes two slots 18 and 20 that are substantially parallel to each other or slightly converging, and disposed on either side of the portion 16 in the form of a spherical cap. The slots 18 and 20 pass through the entire thickness of the prosthetic plate 14. Preferably, each slot 18, 20 comprises a middle portion 18a, 20a with parallel walls, and two end portions respectively 18b & 18c and 20b & 20c of greater width.

Figure 3A:
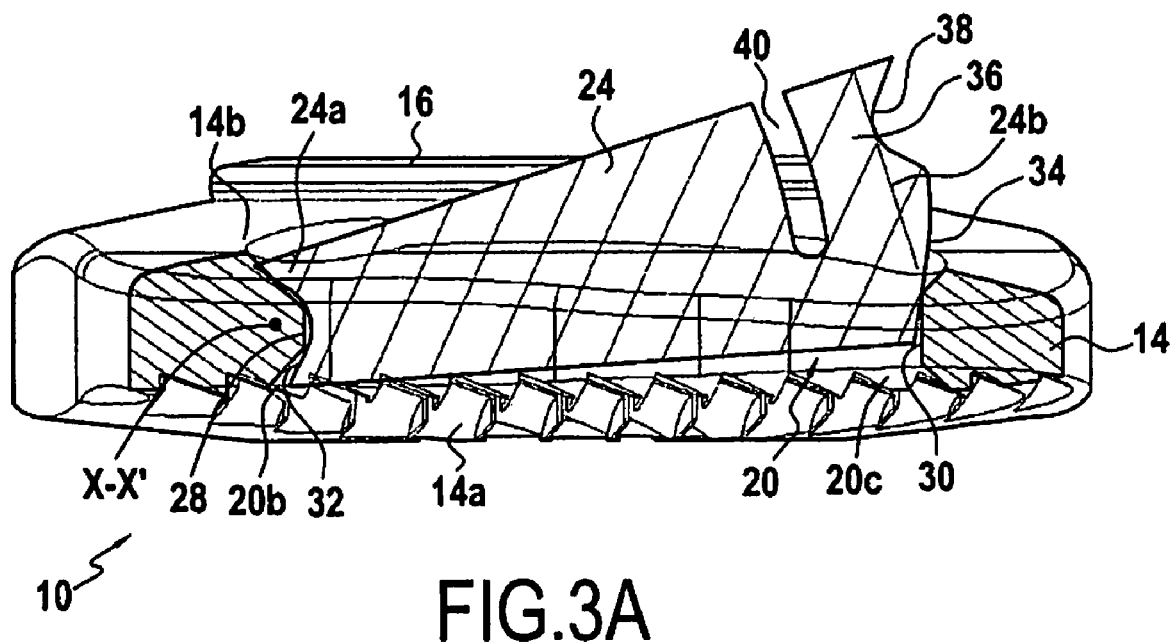
FIG. 3A is a section view on line III-III of FIG. 1 showing the anchor member in the rest position.

With reference to FIG. 3A, there follows a more detailed description of the shape of the slot 20, the slot 18 being identical thereto. An anchor member 24 is mounted in the slot 20 in its long direction, with an anchor member 24 being mounted in the slot 18. The first end 20b of the slot 20 presents a wall portion that, in right section, presents the shape of a generally convex polygonal outlet 28. The other end 20c of the slot presents a wall portion 30 that is substantially rectilinear. With reference to the anchor member 24, it has a first end 24a of profile 32 that is concave for co-operating with the convex profile 28 of the corresponding portion of the wall of the slot 20. The particular shapes of the wall portion of the slot and of the profile at the second end of the anchor member 24 substantially define a pivot axis XX' that is orthogonal to the long direction of the slot 20. The second end 24b of the anchor member 24 has a profile that defines a substantially rectilinear first portion 34 forming a first holding zone, and a second portion 36 having a recess 38 forming a second holding zone. In the zone of the second profile portion 36, the anchor member 24 presents a slot 40 conferring a certain amount of resilience to the second profile portion. As can also be seen in FIG. 3A, the height of the anchor member 24, i.e. its dimension in the height direction of the slot 20, increases going from its first end 24a to its second end 24b, the anchor member being generally triangular in shape. In addition, the thickness of the anchor member 24 is substantially constant and slightly less than the width e of the middle portion 20a of the slot 20. This middle portion 20a serves to guide the anchor member 24 while pivoting about the pivot axis XX', as explained below.

In the position shown in FIG. 3A, the anchor member 24 is in its rest position, i.e. it does not project into the anchor face 14a of the prosthetic plate 14. Naturally, it does project from the other face 14b of the prosthetic plate. In this position, the portion 34 of the anchor member co-operates with friction against the portion 30 of the wall of the slot 20 so as to hold the anchor member 24 in the rest position shown in FIG. 3A. This friction temporarily wedges the anchor member 24 in the slot 20 of the prosthetic plate 14, thereby enabling the surgeon to handle the prosthetic element 10 without the anchor member 24 moving.

Figure 3B:
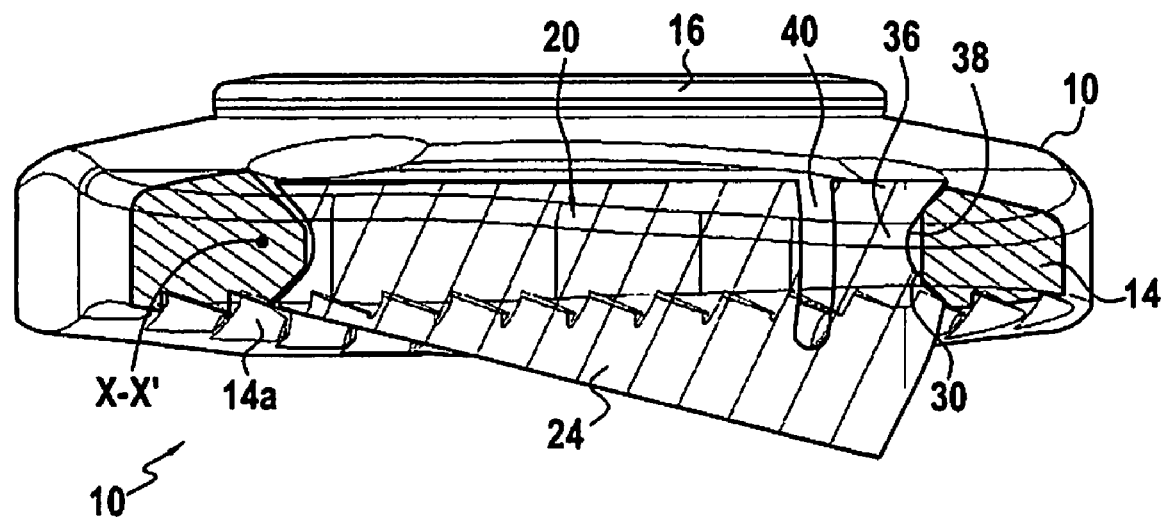
FIG. 3B is a view similar to that of FIG. 3A, but showing the anchor member in the active position.

FIG. 3B shows the anchor member 24 in its active position, i.e. in its position in which it projects from the anchor face 14a of the prosthetic plate. The anchor member is moved by the surgeon into this position by pivoting about the axis XX'. Because of the presence of the slot 40, which confers a certain amount of resilience to the second portion 36 at the second end of the anchor member, the surgeon can bring the anchor member into the position shown in FIG. 3B by deforming the second end of the anchor member. In this position, the recess 38 co-operates with the portion 30 of the end wall of the slot 20, thereby effectively locking the anchor member 24 in its active position.

Thus, the anchor member is held in its rest position by friction means, and in its active position by elastic deformation and snap-fastener means.

Figure 2:
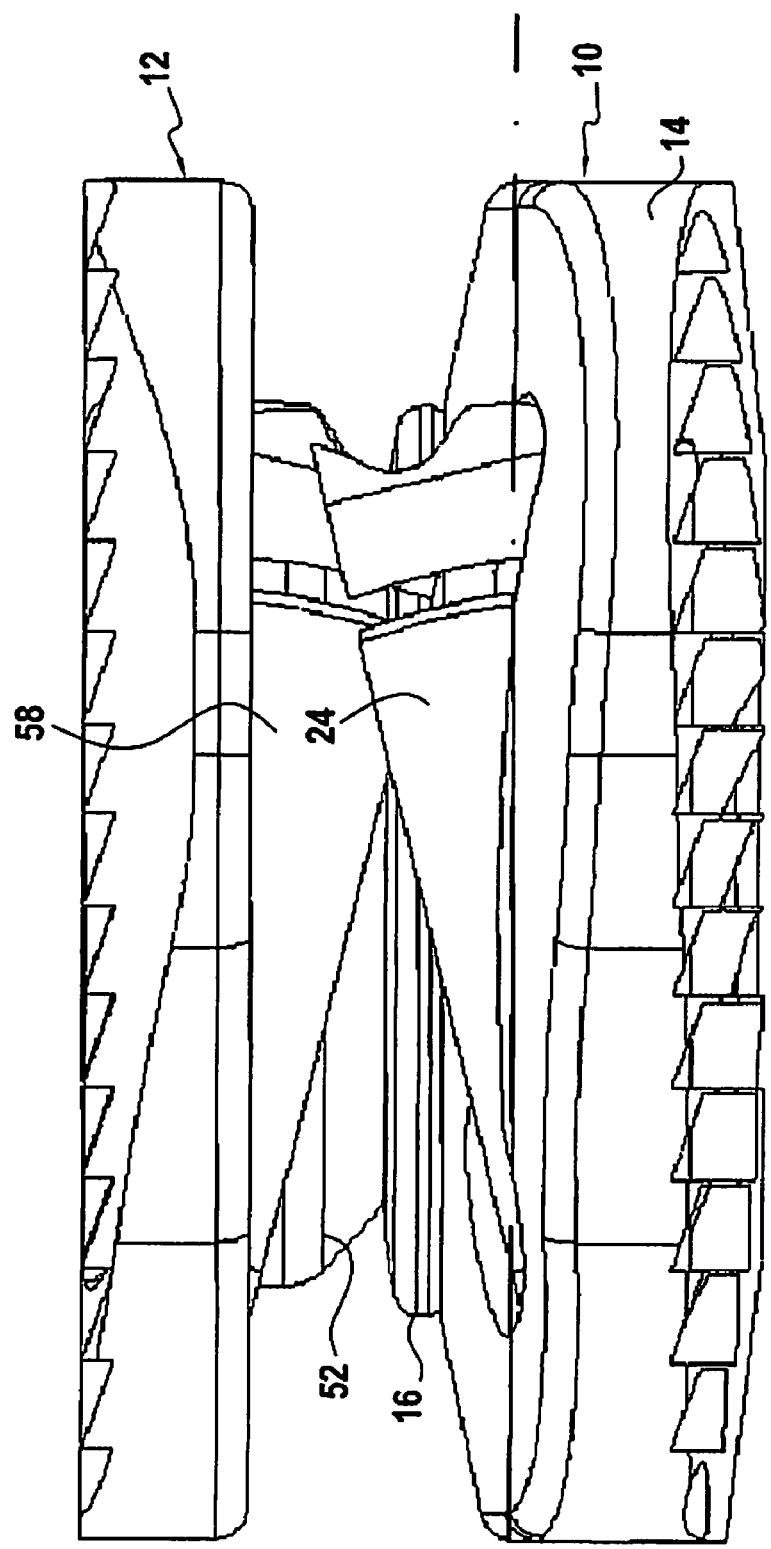
FIG. 2 is a side view in perspective showing the prosthesis as a whole with the anchor members in the rest position.
Figure 5:
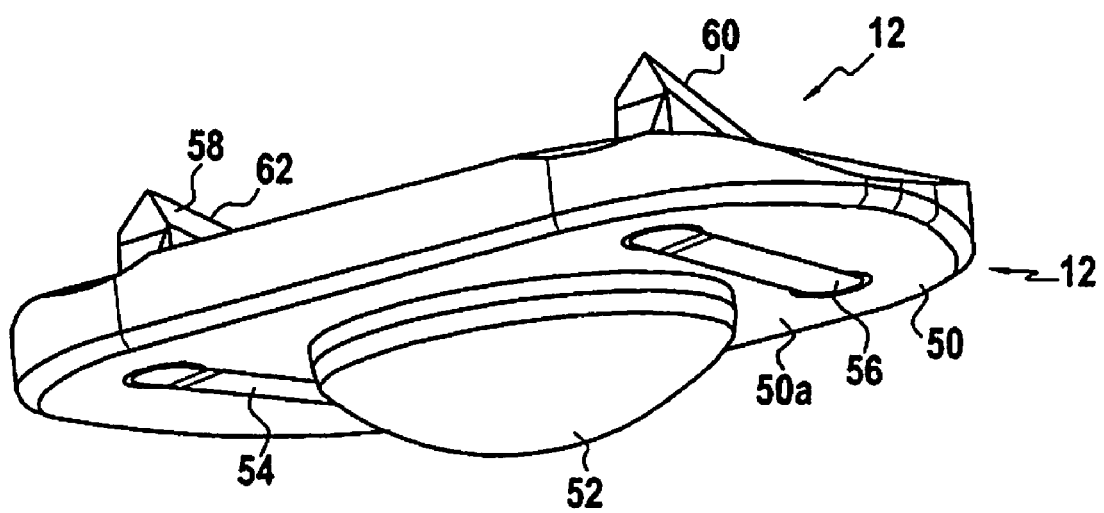
FIG. 5 is a perspective view of the top prosthesis element, the anchor members being in the active position.

FIG. 5 shows the top prosthesis element 12. It comprises a prosthetic plate 50 having a co-operation face 50a that defines a convex spherical cap portion 52 suitable for co-operating with the concave spherical cap portion 16 of the prosthesis element 10. In the prosthetic plate 50, there are formed two parallel slots 54 and 56 identical to the slots 18 and 20 of the prosthesis element 10 and serving to receive anchor members 58 and 60, these anchor members being identical to the anchor members 24 of the bottom prosthesis element 10. Naturally, the slots 54 and 56 are offset relative to the slots 18 and 20 of the bottom prosthesis element 10, as can be seen more clearly in FIG. 2. Thus, the two prosthesis elements 10 and 12 can both have their anchor members 24 and 58, 60 simultaneously in the rest position, with the surfaces constituting spherical cap portions 16 and 52 being in co-operation.

As shown better in FIG. 5, the edges of the anchor members 24, 58, 60 for penetrating into the vertebral plate are chamfered so as to form sharp edges 62.

In the description above, the prosthesis elements both comprise respective single pieces, i.e. it is the same piece that constitutes the prosthetic plate and the spherical cap portions. Naturally, it would not go beyond the invention for each prosthesis element to be made up of a prosthetic plate together with an insert respectively defining the concave spherical cap portion or the convex spherical cap portion.

Figure 4:
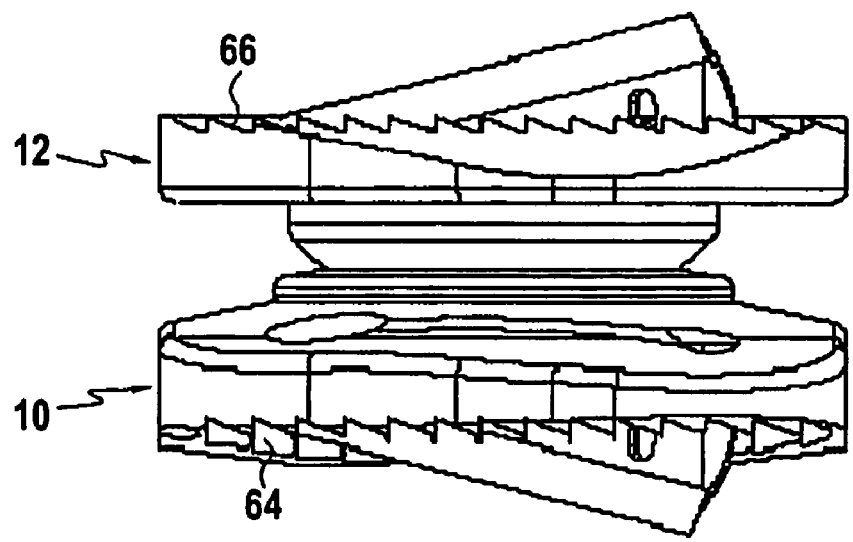
FIG. 4 is an overall view of the prosthesis showing the anchor members in the active position.

As shown in the figures, it should be added that the anchor means of the prosthesis elements 10 and 12 for anchoring in the vertebral plate are essentially constituted by the movable anchor members 24, 58, and 60. Nevertheless, in order to further improve the anchor effect, serrations such as the serrations 64 and 66 shown by way of example in FIG. 4 could be provided in the anchor faces of the prosthetic plate.

It should be emphasized that the anchor means of the invention constituted by the moving anchor members 24 and 58, 60 make it possible effectively to reduce the thickness of the prosthesis elements compared with the thickness they would have when used with anchor members having the same effectiveness but of known type. As shown for example in FIG. 2, when the anchor members 24, 58, 60 are in their rest position they do not project out from the anchor faces of the prosthetic plates, but project from the co-operation faces of those two prosthetic plates. However, the fact that they project from the co-operation faces at rest is not an impediment, since in any event the prosthetic plates are fitted on these faces with structures respectively defining the concave spherical cap 16 and the convex spherical cap 52. In their rest position, the moving anchor members thus do not give rise to any extra thickness compared with the thickness of the prosthesis elements themselves.

The invention claimed is:

1. An intervertebral disk prosthesis comprising:
   a first assembly comprising a prosthetic plate having a fastener face provided with anchor members for anchoring in a vertebra; and
   a second assembly comprising a prosthetic plate having a fastener face provided with anchor members for anchoring in another vertebra;

wherein each anchor member comprises:
a slot formed in a prosthetic plate and passing right through it;
an anchor element mounted on said slot, said anchor element having at least a portion of size greater than the height of said slot;
a means for forming a pivot axis XX' for pivoting said anchor element relative to the prosthetic plate, whereby said anchor element can be moved from a rest, first position in which said anchor element does not project from the fastener face of the prosthetic plate, towards an active, second position in which at least a portion of said anchor element projects from the fastener face of the prosthetic plate;
a first holder means for holding in said first position; and
a second holder means for holding in said second position, wherein the anchor element has a second end having said first and second holder means, and a first end shaped to co-operate with a portion of the wall of said slot to define said means forming the pivot axis XX', wherein the second end of the anchor element has a first portion suitable for co-operating by wedging with a second portion of the wall of said slot opposite from the portion defining the means forming the pivot axis and forming said first holder means, and a second portion that is elastically deformable defining a recess suitable for co-operating with said second portion of the wall of the slot to form the second holder means.

2. A prosthesis according to claim 1, wherein the anchor element is of substantially constant thickness in the direction of the means forming the pivot axis XX', and
wherein the anchor element presents a dimension in the height direction of the slot that decreases going from its second end towards its first end.

3. A prosthesis according to claim 1, wherein each prosthetic plate has two parallel slots and two movable anchor elements mounted respectively in said slot.

4. A prosthesis according to claim 1, wherein the first end of the anchor element includes a concave portion suitable for co-operating with the second portion of the wall of the slot which is of convex shape defining the means forming the pivot axis XX'.

5. An intervertebral disk prosthesis, comprising:
a first plate for engaging a first vertebral body, said first plate comprising a first slot formed through the first plate and a concave spherical cap portion on one side of the first plate;
a second plate for engaging a second vertebral body, said second plate comprising a second slot formed through the second plate and a convex spherical cap portion on one side of the second plate;
a first anchor member, said first anchor member positioned and slidable through the first slot and having a sharp edge for penetrating into the first vertebral body;
a means for forming a pivot axis XX' for pivoting said first anchor member relative to the first plate, whereby said first anchor member can be moved from a rest, first position in which said first anchor member does not project from a face of the first plate, towards an active, second position in which at least a portion of said first anchor member projects from the face of the first plate;
a first holder means for holding in said first position;
a second holder means for holding in said second position, wherein the first anchor member has a second end having said first and second holder means, and a first end shaped to co-operate with a portion of the wall of said first slot to define said means forming the pivot axis XX', wherein the second end of the first anchor member has a first portion suitable for co-operating by wedging with a second portion of the wall of said first slot opposite from the portion defining the means forming the pivot axis and forming said first holder means, and a second portion that is elastically deformable defining a recess suitable for co-operating with said second portion of the wall of the first slot to form the second holder means;
a second anchor member, said second anchor member positioned and slidable through the second slot and having a sharp edge for penetrating into the second vertebral body;
wherein the concave spherical cap portion engages with the convex spherical cap portion to provide relative movement between the first plate and the second plate when the concave spherical cap portion is engaged with the convex spherical cap portion.

6. The prosthesis of claim 5, wherein the sharp edge of the first anchor member is chamfered.

7. The prosthesis of claim 5, wherein the first anchor member is generally triangular in shape.

8. The prosthesis of claim 5, wherein the first anchor member is frictionally fit into the first slot, thereby enabling a surgeon to handle the prosthesis without the first anchor member moving.

9. The prosthesis of claim 5, wherein the first plate comprises a third slot formed through the first plate;
wherein the second plate comprises a fourth slot formed through the second plate;
wherein the prosthesis further comprises a third anchor member, said third anchor member positioned and slidable through the third slot and having a sharp edge for penetrating into the first vertebral body;
wherein the prosthesis further comprises a fourth anchor member, said fourth anchor member positioned and slidable through the fourth slot and having a sharp edge for penetrating into the second vertebral body.

10. The prosthesis of claim 9, wherein the first slot is parallel to the third slot.

11. An intervertebral disk prosthesis, comprising:
a first plate for engaging a first vertebral body, said first plate comprising a first slot formed through the first plate;
a second plate for engaging a second vertebral body, said second plate comprising a second slot formed through the second plate;
a first anchor member, said first anchor member positioned and slidable through the first slot and having a sharp edge for penetrating into the first vertebral body;
a means for forming a pivot axis XX' for pivoting said first anchor member relative to the first plate, whereby said first anchor member can be moved from a rest, first position in which said first anchor member does not project from a face of the first plate, towards an active, second position in which at least a portion of said first anchor member projects from the face of the first plate;
a first holder means for holding in said first position;
a second holder means for holding in said second position, wherein the first anchor member has a second end having said first and second holder means, and a first end shaped to co-operate with a portion of the wall of said first slot to define said means forming the pivot axis XX', wherein the second end of the first anchor member has a first portion suitable for co-operating by wedging with a second portion of the wall of said first slot opposite from the portion defining the means forming the pivot axis and forming said first holder means, and a second portion that is elastically deformable defining a recess suitable for co-operating with said second portion of the wall of the first slot to form the second holder means;

a second anchor member, said second anchor member positioned and slidable through the second slot and having a sharp edge for penetrating into the second vertebral body;

wherein the first plate and the second plate engage with one another by way of complimentary concave and convex spherical cap portions to provide relative movement between the first plate and the second plate.

12. The prosthesis of claim 11, wherein the sharp edge of the first anchor member is chamfered.

13. The prosthesis of claim 11, wherein the first anchor member is generally triangular in shape.

14. The prosthesis of claim 11, wherein the first anchor member is frictionally fit into the first slot, thereby enabling a surgeon to handle the prosthesis without the first anchor member moving.

15. The prosthesis of claim 11, wherein the first plate comprises a third slot formed through the first plate;

wherein the second plate comprises a fourth slot formed through the second plate;

wherein the prosthesis further comprises a third anchor member, said third anchor member positioned and slidable through the third slot and having a sharp edge for penetrating into the first vertebral body;

wherein the prosthesis further comprises a fourth anchor member, said fourth anchor member positioned and slidable through the fourth slot and having a sharp edge for penetrating into the second vertebral body.

16. The prosthesis of claim 15, wherein the first slot is parallel to the third slot.

* * * * *